US011627923B2

(12) United States Patent
Smith et al.

(10) Patent No.: US 11,627,923 B2
(45) Date of Patent: Apr. 18, 2023

(54) CANNULA WITH IMAGE MARKERS TO INDICATE EXPANDABLE SIZE DEVICE

(71) Applicant: Medtronic Holding Company Sàrl, Tolochenaz (CH)

(72) Inventors: Michael A. Smith, San Jose, CA (US); Samuel Lee, San Francisco, CA (US); Emily Benson, Ojai, CA (US)

(73) Assignee: MEDTRONIC HOLDING COMPANY SARL, Tolochenaz (CH)

( * ) Notice: Subject to any disclaimer, the term of this patent is extended or adjusted under 35 U.S.C. 154(b) by 994 days.

(21) Appl. No.: 16/411,820

(22) Filed: May 14, 2019

(65) Prior Publication Data
US 2019/0261933 A1    Aug. 29, 2019

Related U.S. Application Data

(62) Division of application No. 13/773,227, filed on Feb. 21, 2013, now Pat. No. 10,342,498.

(51) Int. Cl.
*A61B 17/34* (2006.01)
*A61B 6/12* (2006.01)
(Continued)

(52) U.S. Cl.
CPC ............ *A61B 6/12* (2013.01); *A61B 17/3439* (2013.01); *A61B 17/3472* (2013.01); *A61B 17/8819* (2013.01); *A61B 6/485* (2013.01); *A61B 2017/3486* (2013.01); *A61B 2090/3966* (2016.02)

(58) Field of Classification Search
CPC .......... A61M 25/0105; A61M 25/0108; A61B 17/3439; A61B 17/3472; A61B 17/88; A61B 17/8802; A61B 17/8811; A61B 17/8819
See application file for complete search history.

(56) References Cited

U.S. PATENT DOCUMENTS

2005/0090852 A1* 4/2005 Layne .................. A61F 2/4601
604/103.05
2006/0264896 A1* 11/2006 Palmer ............... A61B 17/3421
604/164.01

(Continued)

FOREIGN PATENT DOCUMENTS

WO          0004839 A1    2/2000

OTHER PUBLICATIONS

International Search Report and Written Opinion for PCT/2014/017084, the counterpart application dated Jun. 3, 2014.

*Primary Examiner* — Anu Ramana
(74) *Attorney, Agent, or Firm* — Sorell, Lenna & Schmidt, LLP

(57) ABSTRACT

A cannula and method include a shaft portion having a proximal end, a distal end, a longitudinal axis and a lumen extending from the proximal end to the oppositely disposed distal end along the longitudinal axis. A hub is attached to the proximal end of the shaft portion and includes a transverse portion, which extends transversely relative to the longitudinal axis of the shaft portion. An opaque marker is disposed on the transverse portion at a position corresponding to an expanded size of an expandable element such that the opaque marker indicates the expanded size in an imaging system image.

20 Claims, 6 Drawing Sheets

(51) Int. Cl.
*A61B 17/88* (2006.01)
*A61B 6/00* (2006.01)
*A61B 90/00* (2016.01)

(56) References Cited

U.S. PATENT DOCUMENTS

| | | |
|---|---|---|
| 2010/0249817 A1 | 9/2010 | Mark |
| 2011/0172674 A1 | 7/2011 | Bankoski et al. |
| 2011/0202065 A1* | 8/2011 | Takizawa ........... A61B 17/3472 606/94 |
| 2012/0010713 A1* | 1/2012 | O'Halloran ........ A61B 17/7097 623/17.12 |
| 2012/0296161 A1 | 11/2012 | Wallace et al. |
| 2013/0013007 A1 | 1/2013 | Broome et al. |

* cited by examiner

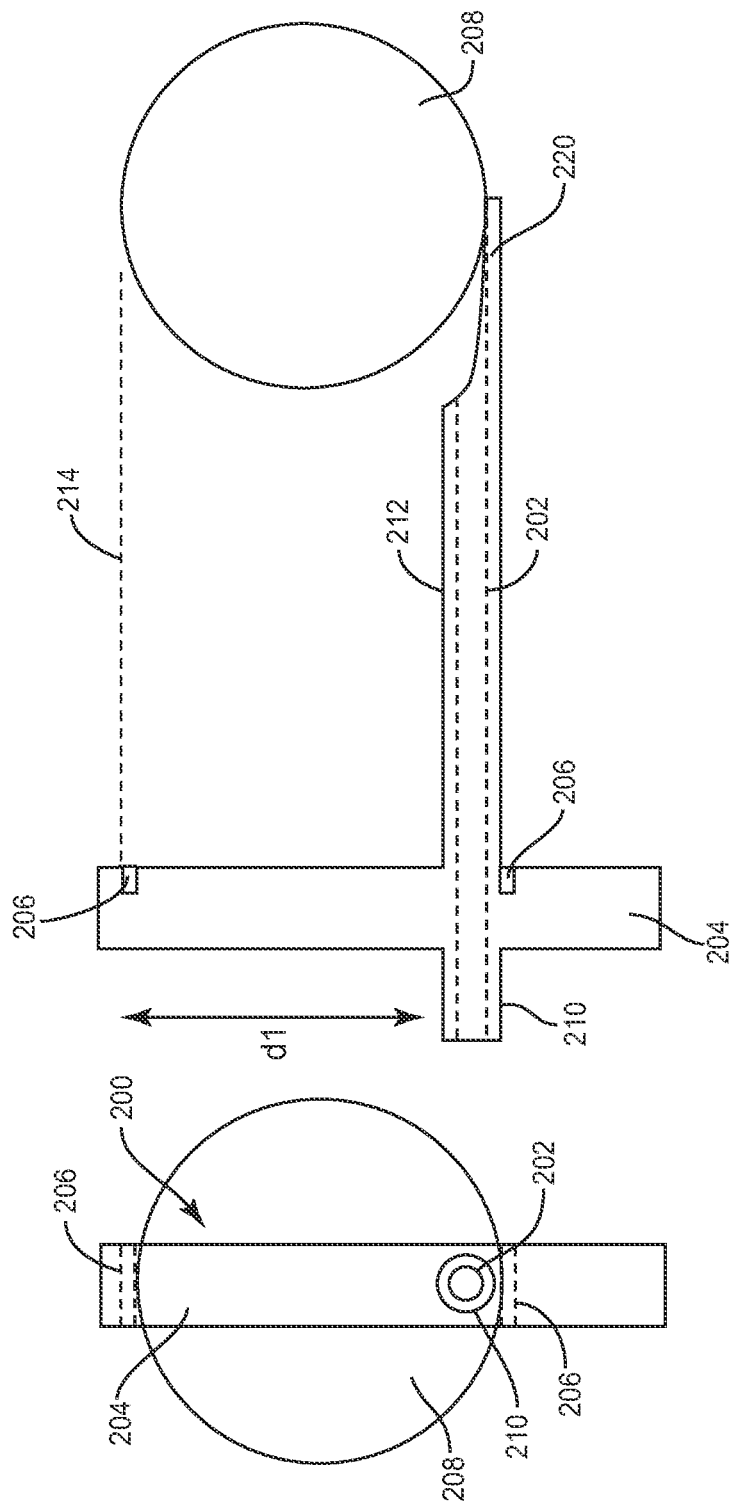

CANNULA WITH IMAGE MARKERS TO INDICATE EXPANDABLE SIZE DEVICE

CROSS-REFERENCE TO RELATED APPLICATIONS

This application is a division of application U.S. patent application Ser. No. 13/773,227, filed on Feb. 21, 2013, which is expressly hereby incorporated by reference herein, in its entirety.

TECHNICAL FIELD

The present disclosure provides cannulas for use in surgical procedures and, more particularly, to a cannula configured with markers to indicate an extent of balloon inflation in medical images. Methods of using such a cannula are also provided.

BACKGROUND

During minimally invasive surgical procedures, cannulas are utilized to provide an access port for surgical instruments and for treating conditions such as fractures. A sharp trocar may be positioned within the cannula and utilized to puncture or pierce the tissue to access damaged bone. Thereafter, the trocar may be removed, leaving the cannula in place providing the access port to the site of treatment. Stabilization of the cannula during treatment is very important, as the ports can be accidentally ejected from the patient or moved while materials, such as bone cement, are being delivered resulting in less perfect treatment and increased procedure time.

Where there is minimal cancellous bone, such as a distal radius, when the cannula is inserted, it cannot be easily stabilized and may not remain stationary. This destabilization can cause imprecise disbursement of material, such as bone cement. In addition, during a procedure, instruments inserted into a patient may not always be visible to ensure proper alignment with instruments and/or anatomical features.

SUMMARY

This application relates to cannula systems and methods of use. In accordance with the present principles, a cannula system includes a shaft portion having a proximal end, a distal end, a longitudinal axis and a lumen extending from the proximal end to the oppositely disposed distal end along the longitudinal axis. A hub is attached to the proximal end of the shaft portion and includes a transverse portion, which extends transversely relative to the longitudinal axis of the shaft portion. An opaque marker is disposed on the transverse portion at a position corresponding to an expanded size of an expandable element such that the opaque marker indicates the expanded size in an imaging system image.

In another embodiment, a cannula includes a shaft portion having a proximal end, a distal end, a longitudinal axis and a lumen extending from the proximal end to the oppositely disposed distal end along the longitudinal axis, the shaft portion including a scoop formed at the distal end for supporting a balloon. A hub is attached to the proximal end of the shaft portion and includes a transverse portion, which extends transversely relative to the longitudinal axis of the shaft portion. Radiopaque markers are disposed on the transverse portion at positions corresponding to an expanded size of the balloon wherein one of the markers is located on the hub at a position corresponding to the scoop of the shaft portion and another marker is located on the hub at a position corresponding to an opposite side of the balloon from the scoop such that the radiopaque markers indicate the expanded size in an imaging system image. One or more holes are formed through the hub in the longitudinal direction, and the holes are configured to receive a stabilizing device.

A treatment method includes providing a cannula having a shaft portion having a proximal end, a distal end, a longitudinal axis and a lumen extending from the proximal end to the oppositely disposed distal end along the longitudinal axis; a hub attached to the proximal end of the shaft portion and including a transverse portion which extends transversely relative to the longitudinal axis of the shaft portion; and at least one opaque marker disposed on the transverse portion at a position corresponding to an expanded size of an expandable element; aligning the expandable element with the shaft portion; expanding the expandable element to the expandable size; and imaging the hub such that the at least one opaque marker indicates the expanded size in an imaging system image.

BRIEF DESCRIPTION OF THE DRAWINGS

The present disclosure will become more readily apparent from the specific description accompanied by the following drawings, in which:

FIG. 5A is an end view showing an asymmetric cannula hub and a balloon schematically shown to demonstrate marker positions relative to the balloon in accordance with another embodiment;

FIG. 5B is a side view showing the cannula hub and the balloon of FIG. 5A to demonstrate marker positions relative to the balloon, a shaft of the cannula having a scoop support an end of the balloon in accordance with another embodiment;

DETAILED DESCRIPTION

Figure 1:
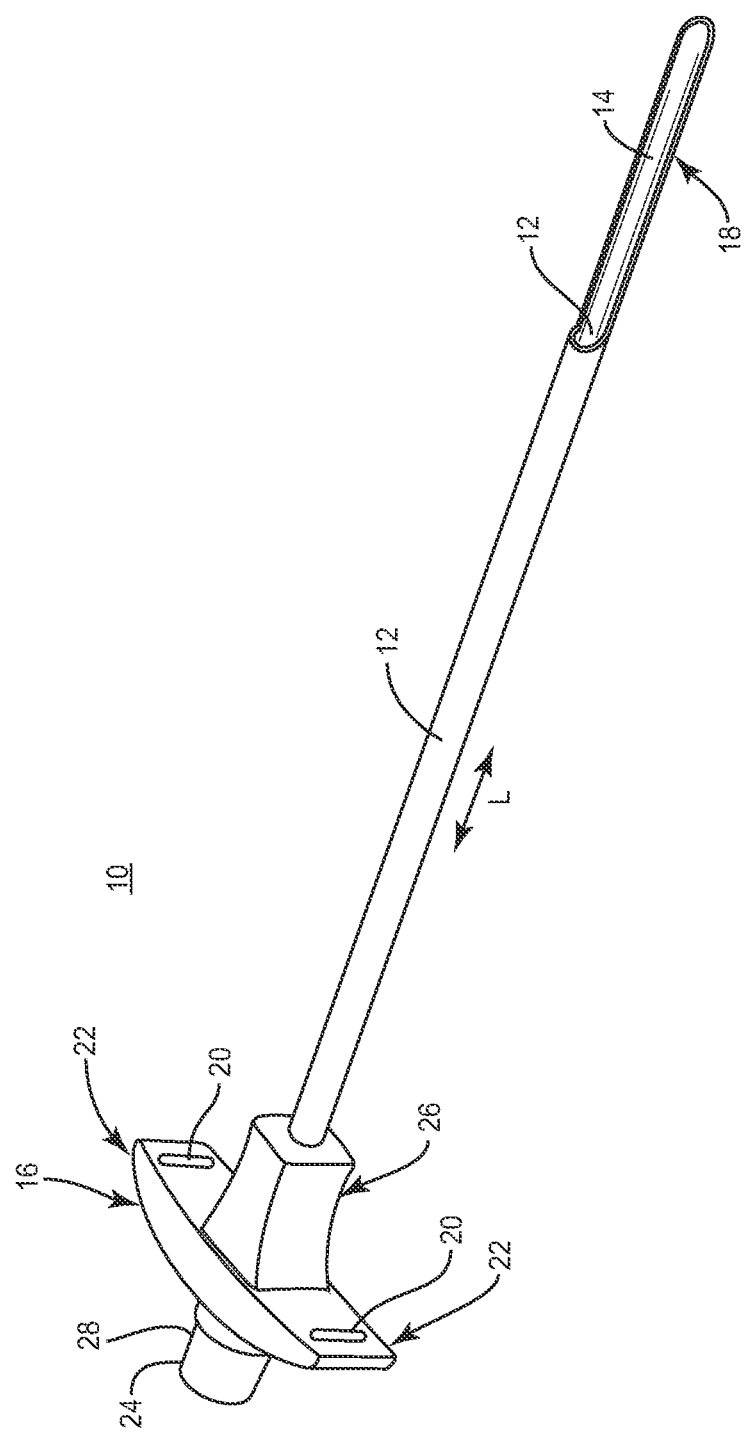
FIG. 1 is a perspective view of a cannula having a scoop formed on a distal end portion in accordance with the principles of the present disclosure.

An apparatus and method are described for a cannula having markers on a handle that indicate a dimension or potential dimension of a balloon employed at a distal end portion of the cannula. For illustrative purposes, the apparatus and method shall be described in the context of positioning expandable balloons in a long bone or vertebra of a patient to treat bone fractures, although the apparatus and methods can be used to treat other conditions.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, distal and proximal, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament and/or bone, repairing a fracture or break in bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a cannula and system for treating fractures, including using an inflatable bone tamp, employing drills and delivering bone void filler, such as, for example, autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables. The disclosure also includes a description of related methods of employing the cannula in accordance with the principles. Alternate embodiments are also disclosed. Reference will now be made in detail to the exemplary embodiments of the present disclosure, which are illustrated in the accompanying figures. Turning now to FIGS. 1-8, there are illustrated components of a cannula device or cannula 10 in accordance with the principles of the present disclosure.

The components of the cannula 10 can be fabricated from biologically acceptable materials suitable for medical apparatuses, including metals, synthetic polymers, ceramics, thermoplastic and polymeric material and/or their composites. For example, the components of the cannula 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix™, Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, polyacrylate and composites of metals and calcium-based ceramics, composites of PEEK and calcium based ceramics, and combinations of the above materials. Various components of the cannula 10 may have material composites, including the above materials, to achieve various desired characteristics such as strength, rigidity, elasticity, compliance, and biomechanical performance, durability and to provide a non-stick surface. The components of the cannula 10 may be monolithically formed, integrally connected or include fastening elements and/or coupling components, as described herein. The cannulas as described herein may be disposable or may be autoclavable or resterilizable. The cannulas and accessories may be part of a kit.

As will be described fully herein, one embodiment of the present disclosure incorporates and utilizes one or more material(s), which exhibit radiopacity. These may include markers or portions of a handle of the cannula 10. Radiopacity refers to the relative inability of electromagnetic radiation, particularly X-rays, to pass through a particular material. Examples of radiopaque materials include, metals, such as stainless steel, titanium, tungsten, or materials that include barium or zirconium, e.g., barium sulfate, zirconium oxide, respectively.

In one embodiment, as shown in FIG. 1, cannula 10 includes a handle portion 26 and a shaft portion 12 extending along a longitudinal axis L. In this embodiment, cannula 10 includes a distal end portion 18 that is formed to resemble a scoop or channel 14. The shaft portion 12 is hollow forming a cavity or lumen 28. A portion of the shaft portion 12 is removed or formed at the end portion 18 to provide the scoop 14. The cavity 28 passes through the entire shaft portion 12 and through a handle portion or hub 26 so that tools and instruments may be threaded therethrough. The handle portion 26 includes an opening at a proximal end portion 24. The proximal end portion 24 forms a port that may be configured to interlock with various tools and instruments for carrying out a procedure. To this end, portion 24 may include various clips, protrusions detents, etc. to mate with and secure the various tools or instruments (e.g., a trocar).

The handle portion 26 includes structures 22 that extend transversely from a longitudinal axis of the shaft portion 12. In accordance with the present principles, the structures 22 are configured and dimensioned to be larger than or equal to a size of a balloon (not shown) at its fully extended position (e.g., the hub 26 or structures 22 will indicate the size of the balloon at maximum inflation volume (MIV). This may be implemented in either uni-directional or omni-directional balloon expansion approaches. In either case, the structures 22 extend outwardly to at least the extend of the MIV or beyond the MIV. Although the structures 22 are depicted as "wings" or bars, the structures 22 may include a plurality of different shapes or combinations of shapes. For example, the structures 22 may include semicircles, may be part of a full circle, may be cylindrical, may be part of a star shape, etc.

Markers 20 are mounted on, detachably connected or integrally formed in the handle portion 26 on the structures 22. A location of the markers 20 may correspond to the MIV of the balloon employed with the cannula 10 during a procedure. It should be understood that the markers 20 might be placed at any other location that provides a beneficial result. In one embodiment, the position of the markers 20 may be adjustable on the structures 22. The markers 20 include radiopaque or other material that creates visibility in images such that during a procedure, the markers 20 will appear in images to indicate a boundary or other distance for a position of the balloon or other instrument to be known. The images may be taken using fluoroscopy, although other imaging techniques (e.g., computed tomography, magnetic resonance, etc.) may be employed. It should be understood that additional markers might be placed on the handle portion 26 as needed or desired.

Figure 2:
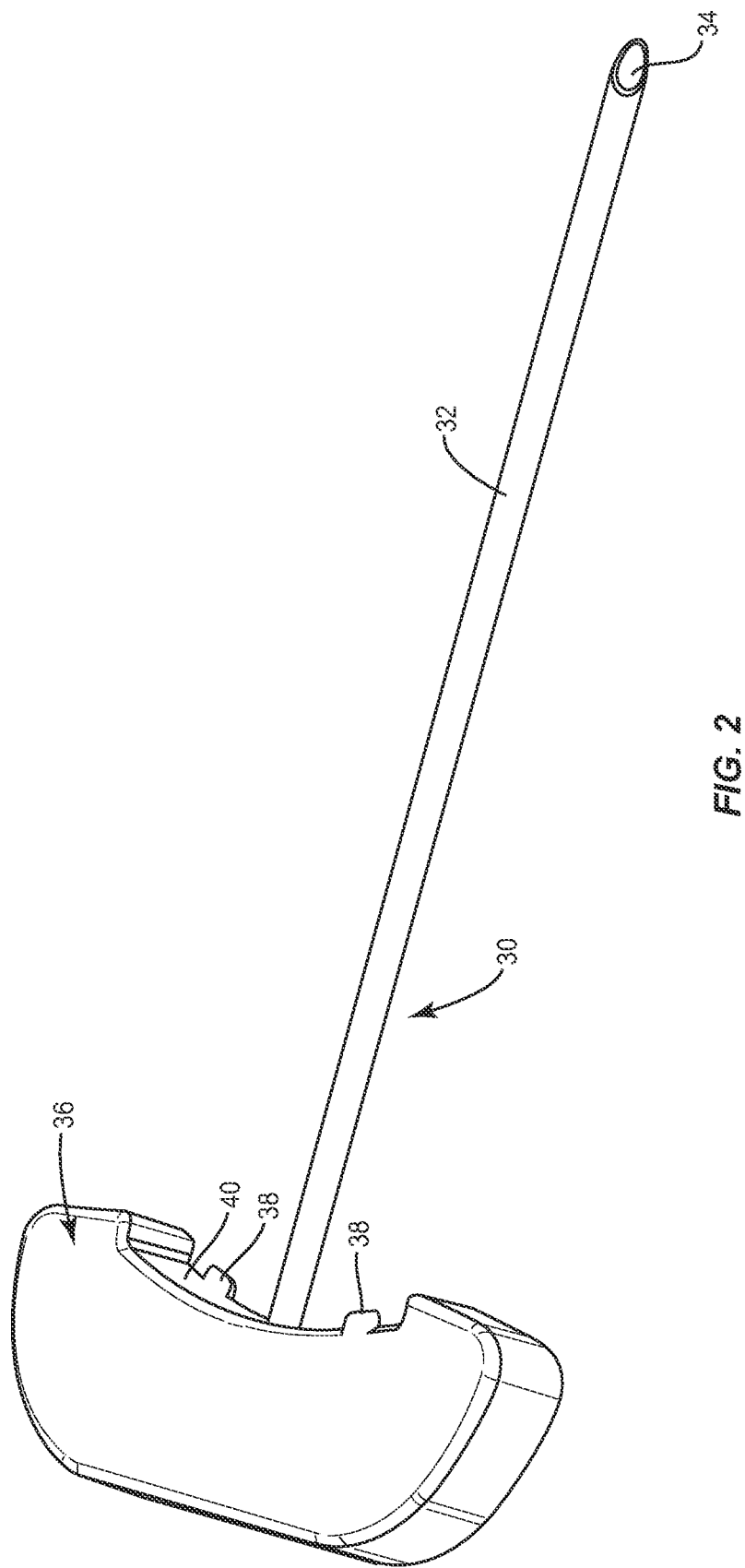
FIG. 2 is a perspective view of a trocar to be employed with the cannula of FIG. 1 in one particular embodiment.
Figure 3:
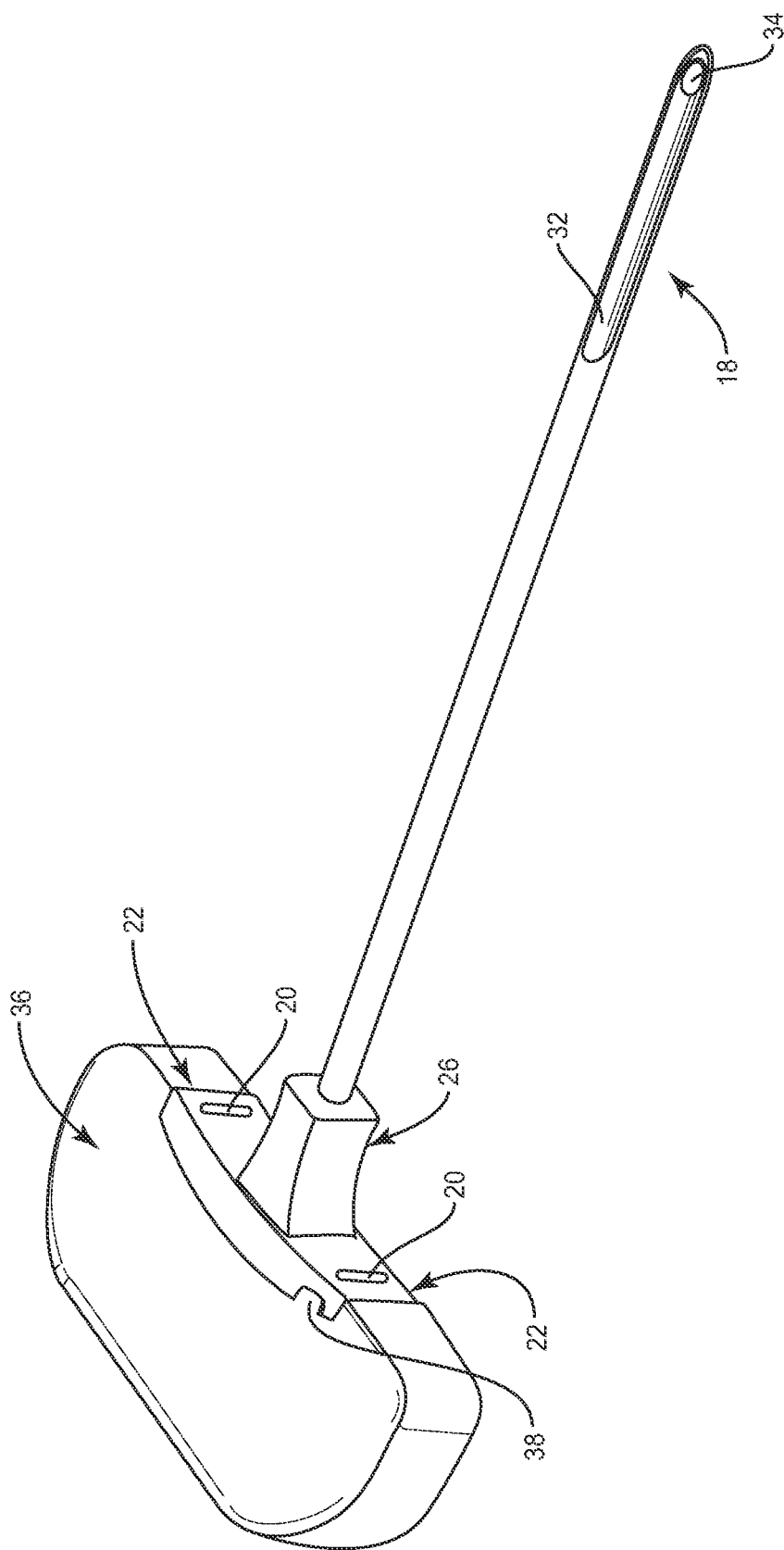
FIG. 3 is a perspective view of the cannula of FIG. 1 having the trocar of FIG. 2 attached thereto in accordance with one illustrative embodiment.

Referring to FIG. 2 with continued reference to FIG. 1, a trocar 30 is illustratively depicted that is configured for use with the cannula 10 depicted in FIG. 1. Trocar 30 is employed for initially piercing tissue to insert the cannula 10 inside a patient. In one embodiment, a solid shaft 32, which includes a pointed end 34, is inserted into the hollow shaft portion 12 of the cannula 10. The shaft 32 is fully inserted into the shaft portion 12 until a surface 16 (FIG. 1) of the handle portion 26 engages a surface 40 of a trocar handle 36. Clips 38 mate with portions of the handle portion 26 to detachably connect the handle portion 26 to the trocar handle 36. The assembled cannula 10 with inserted trocar 30 is depicted in FIG. 3. After the trocar 30 is employed to insert the cannula 10 into the patient, the trocar 30 is removed permitting the cavity 18 to receive other tools or devices. Such tools or devices may include a balloon or the like.

Figures 4A, 4B:
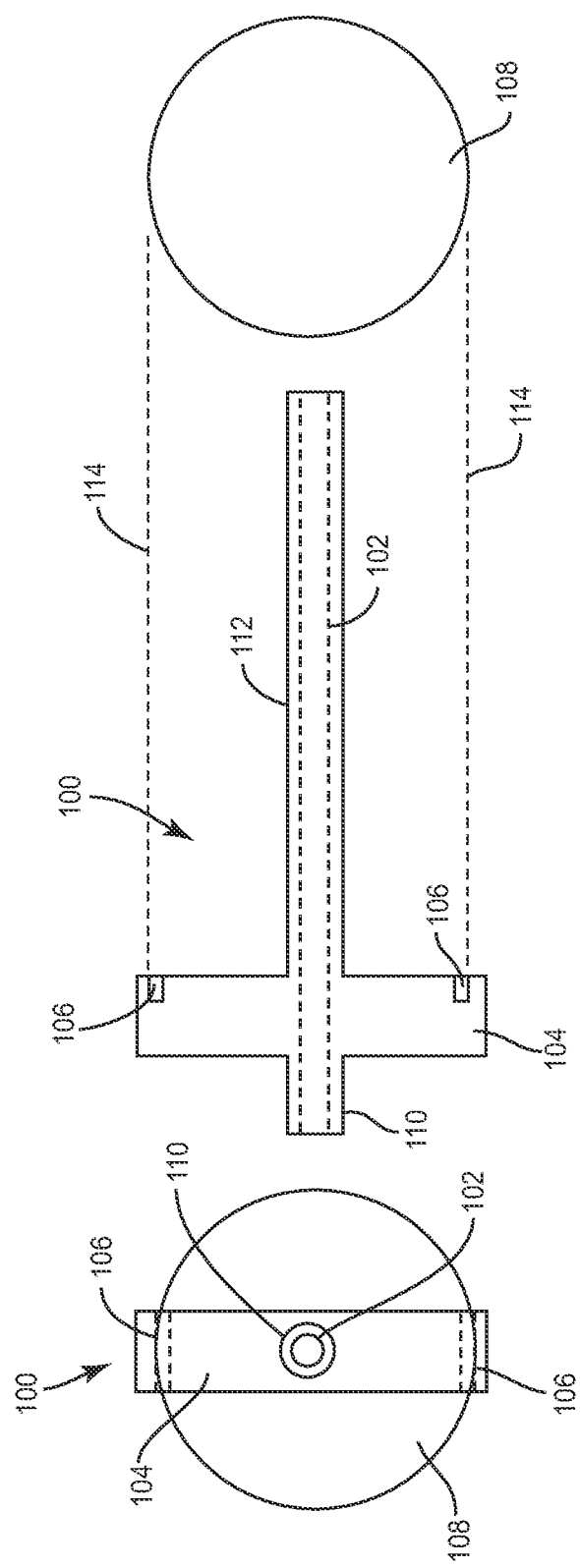
FIG. 4A is an end view showing a cannula hub and a balloon schematically shown to demonstrate marker positions relative to the balloon in accordance with one embodiment.
FIG. 4B is a side view showing the cannula hub and the balloon of FIG. 4A to demonstrate marker positions relative to the balloon in accordance with one embodiment.

Referring to FIGS. 4A and 4B, a proximal end view and a side view of a cannula 100 are respectively shown. FIGS. 4A and 4B include a fully inflated balloon 108 schematically shown to provide a relative measurement as will be described.

FIG. 4A shows a hub or handle portion 104 of the cannula 100 with a balloon 108 schematically depicted at MIV looking in a distal direction longitudinally along a cannula bore 102. The handle portion 104 extends transversely (radially outward) from the cannula bore 102 to a sufficient distance to be equal to or greater than the balloon 108 at MIV. Markers 106 are mounted on or integrally formed in the handle portion 104 at positions corresponding with the MIV position of the balloon 108.

FIG. 4B shows a side view of the cannula 100 with the balloon 108 schematically depicted to demonstrate the positional relationship between boundaries of the balloon 108 and the markers 106. In this embodiment, a shaft 112 does not include a scoop and is uniform about its tip portion. The center of the balloon 108 substantially corresponds with a center of the lumen of the shaft 112. Extents of the balloon 108 at MIV are indicated by lines 114. Balloon expansion is omni-directional in this example.

During a procedure, a trocar (e.g., FIG. 3) may be inserted into the cannula 100, and the system is inserted through tissue to reach, e.g., a bone or other target. The trocar is then removed. The balloon 108, connected to its inflation tube (not shown), may be inserted into a port 110 and fed through the shaft 112. Alternately, the balloon 108 may be inserted through a different port and aligned with the cannula 100. The balloon 108 is positioned and inflated as needed in accordance with the present procedure.

Referring to FIGS. 5A and 5B, a proximal end view and a side view of a cannula 200 are respectively shown. FIGS. 5A and 5B include a fully inflated balloon 208 schematically shown to provide a relative measurement as will be described.

FIG. 5A shows a hub or handle portion 204 of the cannula 200 with a balloon 208 schematically depicted at MIV looking in a distal direction longitudinally along a cannula bore 202. The handle portion 204 extends transversely (radially outward) from the cannula bore 202 to a sufficient distance to be equal to or greater than the balloon 208 at MIV. Markers 206 are mounted on or integrally formed in the handle portion 204 at a position corresponding with the MIV position of the balloon 208.

In this embodiment, cannula 200 includes a scoop 220, which aids in making the balloon 208 uni-directional, e.g., toward a fractured articular surface. The scoop 220 supports the balloon 208, therefore, providing a bound to its lower position. This is in contrast with the approach depicted with omni-directional expansion of the balloon 108 in FIGS. 4A and 4B.

FIG. 5B shows a side view of the cannula 200 with the balloon 208 schematically depicted to demonstrate the positional relationship between boundaries of the balloon 208 and the markers 206. In this embodiment, a shaft 212 includes the scoop 220, such that the center of the balloon 208 is offset from a center of the lumen of the shaft 212. Extents of the balloon 208 at MIV are indicated by a line 214 at an upper position of the balloon 208 at MIV and by the scoop 220 at a lower position of the balloon 208 at MIV. The upper position is offset by a greater distance $d_1$ than the side with the scoop 220 to provide the uni-directional inflation growth of the balloon 208.

In this embodiment, the handle portion 204 is asymmetrically disposed about the cannula bore 202. One marker 206 is located at a lower position of the balloon 208 corresponding with the scoop 220. Another marker 206 corresponds with the upper position indicated by line 214.

During a procedure, a trocar (e.g., FIG. 3) may be inserted into the cannula 200. The trocar is then removed. The balloon 208, connected to its inflation tube (not shown), may be inserted into a port 210 and fed through the shaft 212. Alternately, the balloon 208 may be inserted through a different port and aligned with the cannula 200. The balloon 208 is positioned and inflated as needed in accordance with the present procedure. In this embodiment, the scoop 220 aids in making the balloon 208 uni-directional towards a fractured articular surface or other structure, where the scoop 220 supports the balloon 208. In one particularly useful embodiment, the markers 206 are radiopaque indicators in the hub or handle portion 204 and indicate a maximum inflated diameter of inflatable bone tamps (IBT's) in fluoroscopic images.

Figure 8:
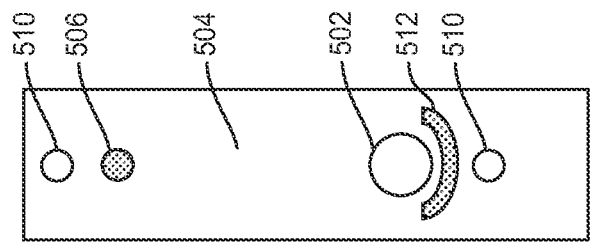
FIG. 8 is an end view showing a cannula hub having asymmetrically disposed markers corresponding to a scoop arrangement for the cannula and having holes configured to receive stabilizing devices, one marker being shaped to provide an orientation of the scoop in accordance with yet another embodiment.
Figure 7:
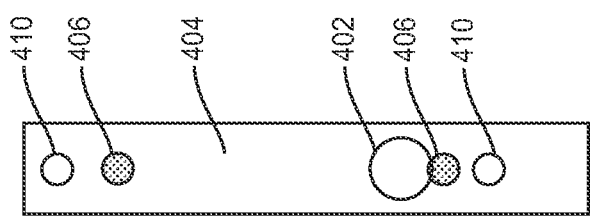
FIG. 7 is an end view showing a cannula hub having asymmetrically disposed markers corresponding to a scoop arrangement for the cannula and holes configured to receive stabilizing devices in accordance with another embodiment.
Figure 6:
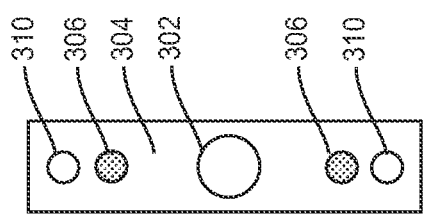
FIG. 6 is an end view showing a cannula hub having symmetrically disposed markers and holes configured to receive stabilizing devices in accordance with one embodiment.

FIGS. 6-8 schematically show different illustrative configurations for the hub or handle portion (e.g., 26, 104, 204) in accordance with the present principles. Referring to FIG. 6, a hub or handle portion 304 includes a cannula bore 302 having markers 306 each disposed an equal distance from the bore 302. The markers 306 may include radiopaque pins, dots, bars, etc. This configuration corresponds to the embodiment where a balloon and the bore 302 have centers that substantially line up when the balloon is inflated (see e.g., hub 104 in FIGS. 4A and 4B). The hub or handle portion 104 includes holes 310 formed therethrough. The holes 310 are configured for receiving a support or stabilization device or structure, such as, e.g., a k-wire. In one embodiment, k-wires may be employed to prevent rotation or movement of the cannula during use. A k-wire or wires (not shown) may be threaded through the holes 310 and attached to bone or other structures to prevent pull-out or rotation of the hub during a procedure.

Referring to FIG. 7, a hub or handle portion 404 includes a cannula bore 402 having markers 406 each disposed an unequal distance from the bore 402. This configuration corresponds to the embodiment, which employs a scoop where a balloon and the bore 402 have centers that are offset when the balloon is inflated (see e.g., hub 204 in FIGS. 5A and 5B). The hub or handle portion 404 includes holes 410 formed therethrough. The holes 410 are configured for receiving a support device or structure, such as, e.g., a k-wire. In one embodiment, k-wires may be employed to prevent rotation or movement of the cannula during use. A k-wire or wires (not shown) may be threaded through the holes 410 and attached to bone or other structures to prevent pull-out or rotation of the hub during a procedure. While FIG. 7 depicts the holes 410 as corresponding to a distance beyond a diameter of an inflated balloon (not shown), holes 410 may be set apart an equal distance from the cannula bore 402. Adjustment of the size of the hub 404 to accommodate this or any other distance desired between the holes 410 may be designed into the hub 404. The holes 410 may have any distance therebetween. In addition, the number of holes 410 need not be two and one or more holes 410 may be employed.

Referring to FIG. 8, a hub or handle portion 504 includes a cannula bore 502 having markers 506 and 512 each disposed an unequal distance from the bore 502. This configuration corresponds to the embodiment, which employs a scoop where a balloon and the bore 502 have centers that are offset when the balloon is inflated (see e.g., hub 204 in FIGS. 5A and 5B). The hub or handle portion 504 includes holes 510 formed therethrough. The holes 510 are configured for receiving a support device or structure, such as, e.g., a k-wire. A k-wire(s) may be employed to prevent rotation or movement of the cannula during use. While FIG. 8 depicts the holes 510 as corresponding to a particular distance, other distances between the holes 510 may be provided. In addition, the number of holes 510 need not be two and one or more holes 510 may be employed. The hub size may be fabricated to accommodate the needed distances between the holes 510.

In this embodiment, the marker 512 is shaped to correspond to a position and shape of the scoop 220 (FIG. 5B). Marker 512 is configured to indicate the position and extent of the scoop portion of the cannula. Marker 512 includes a radiopaque material mounted on or integrated into the hub 504 to show both the maximum inflated diameter of a balloon (or other size) and the scoop cannula configuration such that the marker 512 provides additional information about a position and orientation of the scoop portion in fluoroscopic images. It should be understood that other configurations and shapes of markers may be provided to provide a benefit for a given application. In addition, any number of markers and any shape of marker may be employed in accordance with the present principles.

The cannulas depicted in FIGS. 1-8 may take many forms. It is contemplated that the cannulas may be configured in a number of ways and include different shaped handle portions, such as, for example, round, oval, oblong, square, rectangular, polygonal, irregular, uniform, non-uniform, offset, staggered, tapered, consistent or variable, depending on the requirements of a particular application. An outer surface of the handle portions of the cannulas may be rough, arcuate, undulating, mesh, porous, semi-porous, dimpled and/or textured according to the requirements of a particular application.

Shaft portions of the cannulas may include a lumen that can be variously configured and have a cross-section that is, for example, round, oval, oblong, square, rectangular, polygonal, irregular, uniform, non-uniform, offset, staggered, tapered, consistent or variable, depending on the requirements of a particular application. In one embodiment, in accordance with the disclosure, it is contemplated that the cannulas include a cutting edge at a distal end configured to cut into the tissue. In the alternative, the distal end may include a threaded portion, fluted tip as well as other surgical configurations. In another alternative, a separate device can be used to cut a primary access port for the cannula (e.g., a trocar).

In assembly and use, cannulas are employed in a surgical procedure for treatment of a disorder affecting a section of bone, such as a fracture, for example in the distal radius, tibial plateau or proximal humerus of a patient, as described herein. In use, to treat the affected section, a medical practitioner obtains access to the bone in any appropriate manner, which may include incision and retraction of tissues. Once the bone is exposed the cannula can be used to create and enter an access port adjacent to a fracture to be treated. It is envisioned that cannula may be used in any existing surgical method or technique including open surgery, mini-open surgery, minimally invasive surgery and percutaneous surgical implantation, whereby the site is accessed through a micro-incision, or sleeve that provides a protected passageway to the area. Once access to the surgical site is obtained, the cannula can be deployed so as to deliver an agent, such as bone void filler/bone cement, to treat the condition, such as repair the fracture.

In one particular embodiment, use of the cannula is delivered into the surgical site adjacent to a fracture or a break in a portion of a bone such as the distal radius, tibial plateau or proximal humerus as well as other bone sites. These bone sites have minimal cancellous bone, and therefore, when the cannula is inserted, it cannot be easily stabilized and does not remain stationary. This unstabilization can cause imprecise disbursement of material, such as bone void filler/bone cement. To facilitate stabilization of the cannula, a balloon may be used and when deployed is disposed between an expanded configuration and an unexpanded configuration. When the cannula is inserted into the surgical site, the expanded configuration portion is in its unexpanded configuration within the cannula. As the balloon exits a distal end of the cannula, the expanded configuration is achieved by filling the balloon. The expanded configuration stabilizes the cannula in place by pressing against the existing cancellous bone thereby allowing for precise delivery of bone void filler/bone cement, or deployment of other agents and/or surgical tools that may be required. The scoop portion of the cannula aids in making the expanded unidirectional towards a fractured articular surface. In other words, the scoop supports the expanded balloon in a desired direction. For further stability, k-wires may be employed as described to stabilize the cannula. The balloon is deflated to retract it back into the cannula, and the cannula system can be removed.

It is contemplated that in addition to supporting the expanded balloon in a particular direction, the scoop cannula can be sued to provide bone void filler/bone cement, as well as other to a surgical site. These agents include therapeutic polynucleotides or polypeptides. It is further contemplated that these agents may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite (HA), calcium phosphate and calcium sulfate, biologically active agents, for example, gradual release compositions such as by blending in a bioresorbable polymer that releases the biologically active agent or agents in an appropriate time dependent fashion as the polymer degrades within the patient. Suitable biologically active agents include, for example, Bone Morphogenetic Proteins (BMP), Growth Differentiation Factors (GDF) and cytokines. The components of the cannula can be made to include radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair bone deterioration or damage, in conjunction with the cannula. The marker position may include the MIV of the balloon. However, other positions and reference points may be employed. For example, a half-filled or quarter-filled balloon position may be indicated use the position markers described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A treatment method, comprising:

providing a cannula having a shaft portion having a proximal end, a distal end, a longitudinal axis and a lumen extending from the proximal end to the oppositely disposed distal end along the longitudinal axis, a hub attached to the proximal end of the shaft portion and including a transverse portion which extends transversely relative to the longitudinal axis of the shaft portion, and at least one opaque marker disposed on the transverse portion at a position corresponding to an expanded size of an expandable element;

aligning the expandable element with the shaft portion;

expanding the expandable element to the expanded size; and imaging the hub such that the at least one opaque marker indicates the expanded size in an imaging system image.

2. A method as in claim 1, further comprising a scoop on the distal end of the shaft portion for contacting the expandable element, the at least one opaque marker including two markers, one marker being located on the hub at a position corresponding to the scoop of the shaft portion and another of the two markers being located on the hub at a position corresponding to an opposite side of the balloon from the scoop.

3. A method as in claim 2, wherein the marker located on the hub at the position corresponding to the scoop includes a shape for indicating an orientation of the scoop.

4. A method as in claim 2, wherein the marker located on the hub at the position corresponding to the opposite side of the balloon from the scoop does not overlap the marker located on the hub at the position corresponding to the scoop in a longitudinal direction.

5. A method as in claim 2, wherein:

the marker located on the hub at the position corresponding to the scoop includes a shape for indicating an orientation of the scoop; and the marker located on the hub at the position corresponding to the opposite side of the balloon from the scoop does not overlap the marker located on the hub at the position corresponding to the scoop in a longitudinal direction.

6. A method as in claim 1, further comprising a scoop on the distal end of the shaft portion for contacting the expandable element, the at least one opaque marker including a first marker, a second marker, and a third marker, the first marker being disposed on the transverse portion at the position corresponding to the expanded size of the expandable element, the second marker being located on the hub at a position corresponding to the scoop of the shaft portion, the third marker being located on the hub at a position corresponding to the distal end.

7. A method as in claim 6, wherein the second marker includes a shape for indicating an orientation of the scoop.

8. A method as in claim 6, wherein the first marker, the second marker, and the third marker do not overlap in a longitudinal direction.

9. A method as in claim 6, wherein:

the second marker includes a shape for indicating an orientation of the scoop; and the first marker, the second marker, and the third marker do not overlap in a longitudinal direction.

10. A treatment method, comprising:
providing a cannula comprising:
- a shaft extending along a longitudinal axis between a proximal end and an opposite distal end, the distal end including an end portion forming a scoop,
- a balloon having an outer surface with opposite first and second sides, the first side being supported by the scoop, and
- a hub attached to the proximal end, the hub including a transverse portion extending transverse to the longitudinal axis, the transverse portion including a first marker located at a position corresponding to the scoop, the transverse portion including a second marker located at a position corresponding to the second side; and imaging the hub such that the first marker indicates a position of the scoop in an imaging system and the second marker indicates a position of the second side in the imaging system.

11. A method as in claim 10, wherein the balloon is movable between an unexpanded configuration and an expanded configuration in which the balloon has an expanded size, the second marker being located at the position corresponding to the second side when the balloon is in the expanded configuration.

12. A method as in claim 10, wherein the first marker includes a shape for indicating an orientation of the scoop.

13. A method as in claim 10, wherein the first marker does not overlap the second marker in a longitudinal direction.

14. A method as in claim 10, wherein the markers are fixed relative to the shaft.

15. A method as in claim 10, wherein the markers are each disposed in a transverse plane.

16. A method as in claim 10, wherein the markers create visibilities in the imaging system, the visibilities being spaced apart from one another when viewed along the longitudinal axis.

17. A method as in claim 10, wherein the markers are opaque.

18. A method as in claim 10, wherein the markers are radiopaque.

19. A method as in claim 10, wherein the markers are disposed at substantially equal distances from the shaft.

20. A treatment method, comprising:
providing a cannula comprising:
- a shaft extending along a longitudinal axis between a proximal end and an opposite distal end, the distal end including an end portion forming a scoop,
- a balloon having an outer surface with opposite first and second sides, the first side being supported by the scoop, the balloon is movable between an unexpanded configuration and an expanded configuration in which the balloon has an expanded size, and
- a hub attached to the proximal end, the hub including a transverse portion extending transverse to the longitudinal axis, the transverse portion including a first radiopaque marker located at a position corresponding to the scoop, the first radiopaque marker including a shape for indicating an orientation of the scoop, the transverse portion including a second radiopaque marker located at a position corresponding to the second side when the balloon is in the expanded configuration, the second radiopaque marker not overlapping the first radiopaque marker in a longitudinal direction;

moving the balloon from the unexpanded configuration to the expanded configuration; and imaging the hub such that the first marker indicates a position and orientation of the scoop in an imaging system and the second marker indicates a position of the second side in the imaging system.

\* \* \* \* \*